(12) United States Patent
Jacobsen et al.

(10) Patent No.: US 8,696,336 B2
(45) Date of Patent: Apr. 15, 2014

(54) MINIATURE PUMP DEVICE WITH AN ANTI-FREE FLOW VALVE

(75) Inventors: Stephen C. Jacobsen, Salt Lake City, UT (US); Shane Olsen, Farmington, UT (US)

(73) Assignee: Sterling Investments, LC, Salt Lake City, UT (US)

( * ) Notice: Subject to any disclaimer, the term of this patent is extended or adjusted under 35 U.S.C. 154(b) by 939 days.

(21) Appl. No.: 12/604,237

(22) Filed: Oct. 22, 2009

(65) Prior Publication Data

US 2010/0135831 A1  Jun. 3, 2010

Related U.S. Application Data

(60) Provisional application No. 61/107,597, filed on Oct. 22, 2008.

(51) Int. Cl.
 *F04B 7/00* (2006.01)
(52) U.S. Cl.
 USPC .......................................... 417/446; 137/510
(58) Field of Classification Search
 USPC ............... 251/45; 137/625.25, 494, 495, 510;
  417/44.2, 44.9, 415, 443, 446, 447
 See application file for complete search history.

(56) References Cited

U.S. PATENT DOCUMENTS

| | | | | |
|---|---|---|---|---|
| 2,881,749 A | * | 4/1959 | Pringham | 123/179.12 |
| 3,245,426 A | * | 4/1966 | Kreuter et al. | 137/112 |
| 3,390,919 A | * | 7/1968 | Boyce | 303/31 |
| 3,650,093 A | | 3/1972 | Rosenberg | |
| 3,712,579 A | * | 1/1973 | Murray et al. | 251/38 |
| 4,373,527 A | | 2/1983 | Fischell | |
| 4,981,157 A | * | 1/1991 | Denkinger | 137/510 |
| 5,485,984 A | * | 1/1996 | Itoi et al. | 251/331 |
| 5,607,418 A | | 3/1997 | Arzbaecher | |
| 5,694,919 A | | 12/1997 | Rubsamen et al. | |
| 6,656,159 B2 | | 12/2003 | Flaherty | |
| 6,669,663 B1 | | 12/2003 | Thompson | |
| 6,726,672 B1 | | 4/2004 | Hanly et al. | |
| 7,264,611 B2 | | 9/2007 | Christenson et al. | |
| 7,367,968 B2 | | 5/2008 | Rosenberg et al. | |
| 7,429,255 B2 | | 9/2008 | Thompson | |
| 2003/0121414 A1 | | 7/2003 | Cautenet et al. | |
| 2003/0163089 A1 | | 8/2003 | Bynum | |
| 2003/0229330 A1 | | 12/2003 | Hickle | |
| 2004/0249334 A1 | | 12/2004 | Cull | |
| 2005/0039797 A1 | * | 2/2005 | Carlson | 137/494 |

OTHER PUBLICATIONS

U.S. Appl. No. 12/082,676, filed Apr. 11, 2008; Stephen C. Jacobsen; office action issued Nov. 29, 2010.

(Continued)

*Primary Examiner* — Devon Kramer
*Assistant Examiner* — Amene Bayou
(74) *Attorney, Agent, or Firm* — Bateman IP

(57) ABSTRACT

A miniature unidirectional valve configured to restrict the free flow of fluid through the valve includes a valve body having an inlet and an outlet. A flexible membrane is movably disposed over the inlet and outlet, and movable between an open position and a closed position. The flexible membrane is movable by a pressure from the inlet to move the membrane to the open position. A control chamber is disposed in the valve body adjacent the fluid flow path, and configured to apply a pressure against the membrane to move the membrane to the closed position to restrict fluid flow through the valve. A preload structure is associated with the flexible membrane, and biases the flexible membrane toward the closed position.

9 Claims, 12 Drawing Sheets

(56) References Cited

OTHER PUBLICATIONS www.instechlabs.com, Instech Solomon, Pumps, Pegasus Infusion Pump, 2 pages.
Shimadzu LC-10ADVP, :C-10ADVP micro-piston pump, 1 page.
Archive News Story, "Minature Piston Pump measures 44×17.3×25.5 mm" and Archive Press Release "New Miniature Position Pump Great Solution for Low volume Applications", Feb. 12, 2002, 1 page.
E. Clark & Associates, GOTEC, 5 pages.
Jacobsen, et al., U.S. Appl. No. 12/082,676, filed Apr. 11, 2008.
U.S. Appl. No. 12/082,676, filed Apr. 11, 2008; Stephen C. Jacobsen; office action dated Jul. 20, 2012.
U.S. Appl. No. 12/082,6376, filed Apr. 11, 2008; Stephen C. Jacobsen; notice of allowance dated Dec. 7, 2012.

* cited by examiner

MINIATURE PUMP DEVICE WITH AN ANTI-FREE FLOW VALVE

CROSS-REFERENCE TO RELATED APPLICATIONS

This application claims the benefit of U.S. Provisional Patent Application No. 61/107,597, filed Oct. 22, 2008, and entitled, "Miniature Pump Device and Method," which is incorporated by reference in its entirety herein.

BACKGROUND OF THE INVENTION

1. Field of the Invention

The present invention relates generally to fluid pumps, and more particularly to miniature jack or piston pumps.

2. Related Art

Miniature pumps have been used in a variety of applications such as drug delivery devices, miniature hydraulic systems, and the like. Some miniature pumps flex a diaphragm or use a dragging seal to create a vacuum to move fluid into and out of the pump. Other miniature pumps, such as piston pumps, have to rotate or slide a seal in order to push or impel fluid through the pump. The moving seals in these types of pumps have presented problems in that relatively significant amounts of power are needed in order to overcome resistive frictional forces and move the seals. Consequently, relatively large batteries or other power sources have been required to power these miniature pumps, thereby reducing the size benefit of the miniature pump.

Additionally, very small pumps typically operate at relatively high frequencies. The rapid cycling of pistons, impellors, and seals can wear the seals and cause leakage of the pumped fluid out of the pump. Moreover, high frequency cycling can cause cavitation, or the generation of gas bubbles, within the fluid flow path in the pump. Bubbles in the fluid stream affect the output volume of the pump and affect pump efficiency. Bubbles can also be dangerous to patients when such pumps are used as drug delivery devices.

Such small pumps are often used in applications that may require anti-back flow or anti-free flow measures, such as drug delivery systems. Unfortunately, anti-back flow or anti-free flow valves typically require additional bulky structure coupled to the pump outlet. These types of valves will sometimes limit the size of the reservoir or battery since the size of the overall system is often constrained by the space available for installation of the pump, such as a patient's abdominal cavity in the case of a sub-dermal drug pump.

SUMMARY OF THE INVENTION

It has been recognized that it would be advantageous to develop a miniature pump device for pumping fluid with an anti-free flow valve. It has also been recognized that it would be advantageous to develop a method for controlling the free flow of fluid using an anti-free flow valve.

In one aspect, the present invention provides for a miniature unidirectional valve configured to restrict the free flow of fluid through the valve. The miniature valve can include a valve body having an inlet and an outlet. A flexible membrane can be movably disposed over the inlet and outlet, and movable between an open position and a closed position. The flexible membrane can be movable by a pressure from the inlet to move the membrane to the open position. A control chamber can be disposed in the valve body adjacent the fluid flow path, and configured to apply a pressure against the membrane to move the membrane to the closed position to restrict fluid flow through the valve. A preload structure can be associated with the flexible membrane, and bias the flexible membrane toward the closed position.

In another aspect of the invention, the present invention provides for a miniature pump device with an anti-free flow valve.

The present invention also provides for a method for restricting the free flow of fluid in a fluid delivery system, such as an intravenous drug delivery system, a subdermal drug pump, or the like, including providing a valve body having an inlet, an outlet, and a flexible membrane disposed across the inlet and outlet. The flexible membrane can define a fluid flow path or a blocking member between the inlet and the outlet on one side of the flexible membrane, and a control chamber on an opposite side of the flexible membrane. The fluid flow path can be opened with pressure from the inlet to move the flexible membrane to an open position such that flexible membrane defines an unobstructed fluid flow path between the inlet and outlet to allow fluid to flow between the inlet and the outlet. The fluid flow path can be closed by a pressure against the flexible membrane to move the flexible membrane to a closed position such that the flexible membrane presses against and seals over the outlet to restrict fluid flow therethrough. The flexible membrane can be biased toward the closed position with a preload structure such that closing the fluid flow path requires less pressure than opening the fluid flow path.

Additional features and advantages of the invention will be apparent from the detailed description which follows, taken in conjunction with the accompanying drawings, which together illustrate, by way of example, features of the invention.

DETAILED DESCRIPTION

Figure 1:
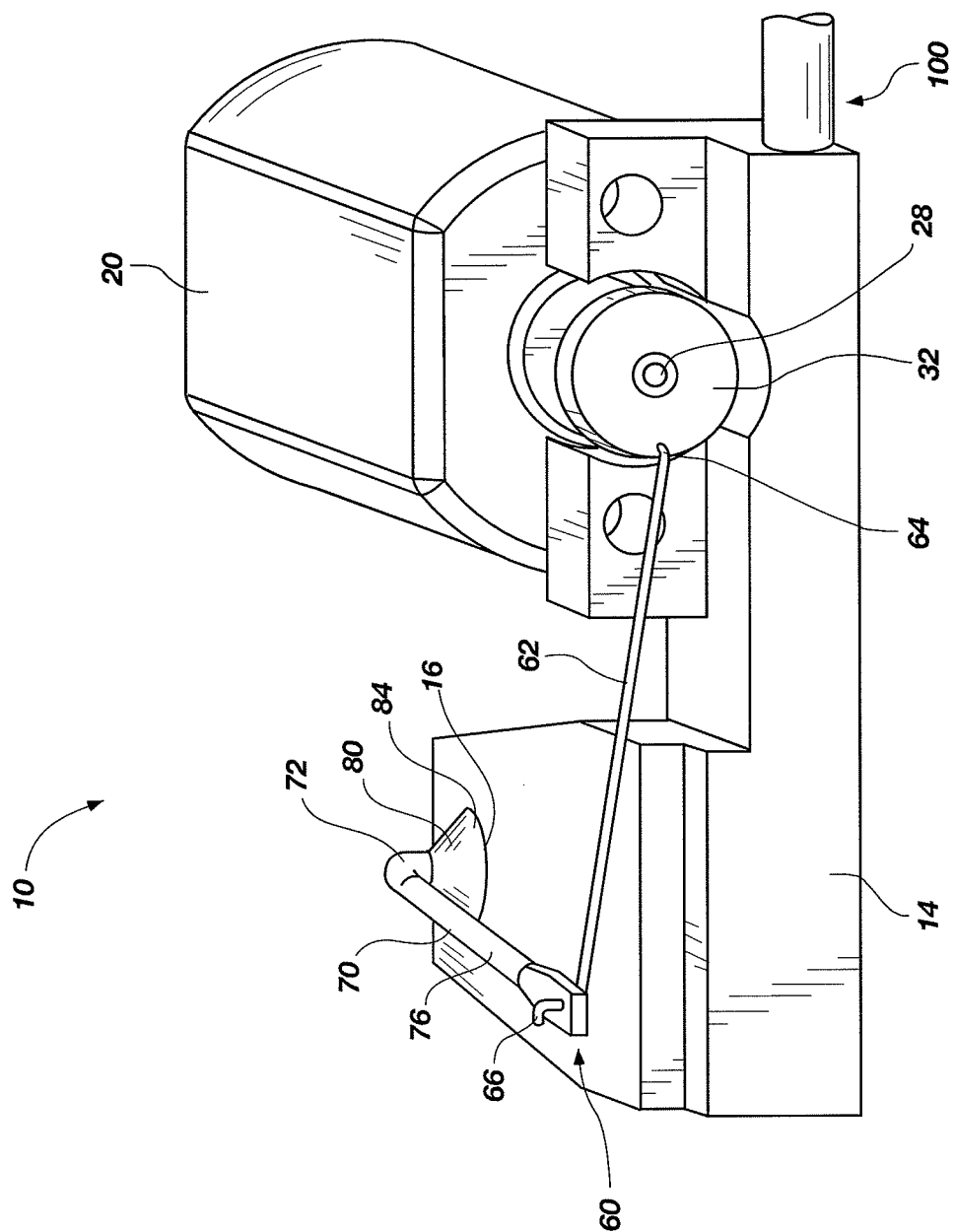
FIG. 1 is a perspective view of a miniature pump device in accordance with one exemplary embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention generally provides for a miniature pump that can be used as a drug delivery device, a miniature hydraulic pump, or the like. The pump has a stationary flexible seal to seal the moving parts of the pump within the fluid reservoir. The pump has a motor outside the fluid reservoir that drives a piston inside the fluid reservoir, which piston functions to pump fluid within the fluid reservoir. A power transfer linkage extends from the motor to the piston and transfers power from the motor to the piston to drive the piston. The stationary flexible seal surrounds a portion of the power transfer linkage and seals against the fluid reservoir to restrict fluid leakage from the reservoir as the power transfer linkage moves. The flexible seal is bonded to the power transfer linkage and flexes around the power transfer linkage during use to maintain the seal around the power transfer linkage. The piston is also configured to restrict the formation of bubbles within the fluid flow path of the pump.

As illustrated in FIGS. 1-4, a miniature pump device, shown generally at 10, is shown in accordance with one exemplary embodiment of the present invention. The miniature pump 10 can have a fluid reservoir 14 that can contain an intravenous drug, hydraulic fluid, or the like. The pump 10 can also have a motor 20 disposed adjacent the fluid reservoir 14, and a piston, shown generally at 100, disposed within the fluid reservoir 14. A power transfer linkage, shown generally at 60, can transfer power from the motor 20 to the piston 100 in the fluid reservoir 14 to pump fluid, and a stationary flexible seal 80 can be coupled between the fluid reservoir 14 and the power transfer linkage 60 to seal a portion of the power transfer linkage 60 within the fluid reservoir 14. Thus, fluid leakage can be restricted by the flexible seal as the motor 20 drives the power transfer linkage 60.

The motor 20 can be a small electrical motor, and a power source 24 (FIG. 4), such as a battery, can be electrically coupled to or otherwise operable with the motor 20. It will be appreciated that an AC or DC motor, or combination thereof, can be used to power the miniature pump 10 along with transformers. The motor 20 can have an output shaft 28 that can rotate a drive wheel 32. The drive wheel 32 can output power from the motor 20 in the form of rotational energy.

A controller 36 (FIG. 4) can be electrically coupled between the power source 24 and the motor 20 to control actuation of the motor 20, and hence operation of the miniature pump 10. It will be appreciated that the controller 36 can include a programmable electronic switch that can precisely control the flow from the pump 10. Additionally, the controller 36 can be a simple on/off switch that can be activated by a user or other activation source.

The power transfer linkage 60 (FIG. 2) can include a flexible rod 62 that can translate rotational energy from the drive wheel 32 of the motor 20 into linear energy to power the linear movement of the piston 100. The flexible rod 62 can have a drive wheel end 64 and a power transfer end 66. The drive wheel end 64 can be pivotally coupled to the drive wheel 32 so that as the drive wheel rotates, the drive wheel end 64 of the flexible rod 62 moves in a circular motion which in turn moves the power transfer end 66 back and forth in a substantially linear motion. The flexible rod 62 can be a thin elastically flexible wire rod that can flex under an applied load from the drive wheel 32 and return to an original shape when no load is applied. Advantageously, the flexible rod 62 eliminates the need for a complex joint between the drive wheel 32 and the U-shaped linkage 70.

A U-shaped linkage 70 can be pivotally coupled to the power transfer end 66 of the flexible rod 62. The U-shaped linkage can have a reservoir arm 74, and an outside arm 76 that each extend from a base 72 to form the U-shaped configuration shown of the linkage 70. The reservoir arm 74 can be at least partially enclosed within the fluid reservoir 14. The outside arm 76 can be outside the fluid reservoir 14. The miniature pump comprises a structural housing that defines the reservoir 14, with the outside arm 76 being positioned outside of the fluid reservoir 14 and the reservoir arm contained within the fluid reservoir 14. The housing further provides support for the motor, piston and other components.

The U-shaped linkage 70 can be mounted to the fluid reservoir 14 such that the U-shaped linkage 70 can pivot about the base 72, and can be oriented in a substantially transverse relationship to the flexible rod 62. The outside arm 76 of the U-shaped linkage 70 can be pivotally coupled to the power transfer end 66 of the flexible rod 62 so that as the power transfer end 66 of the flexible rod 62 moves back and forth as a result of being driven by the motor 20, the outside arm 76 is also caused to move, which movement pivots the U-shaped linkage 70. In addition, as the outside arm 76 is operable with the reservoir arm 74 through the base 72, the reservoir arm 74 is also caused to move or pivot. The reservoir arm 74 can be pivotally coupled to the piston 100 so that as the U-shaped linkage 70 is pivoted back and forth by the motor 20, the reservoir arm 74 moves the piston 100 back and forth.

In one aspect the motor 20 can cycle the power transfer linkage 60 at a frequency greater than 100 Hz. In another aspect, the motor can cycle the power transfer linkage 60 approximately 200 Hz. In this way, the power transfer linkage 60 can translate rotary energy or power from the motor 20 to linear power to drive the piston 100. Thus, the power transfer linkage 60 is an example of one means for transferring power to provide power from the motor 20 to the piston 100 to pump fluid from the fluid reservoir 14.

The flexible seal 80 can be coupled between the fluid reservoir 14 and the power transfer linkage 60. The flexible seal 80 can seal a portion of the power transfer linkage 60 in the fluid reservoir 14 and restrict fluid from escaping from the fluid reservoir 14 as the power transfer linkage 60 moves during use. The flexible seal 80 can be an elastomeric plug 84 disposed in a wall 16 of the fluid reservoir 14, with a portion of the power transfer linkage 60 extending through the elastomeric plug 84. The elastomeric plug 84 can be bonded to the power transfer linkage 60 to form a seal on the power transfer linkage 60. The elastomeric plug 84 can elastically flex as the power transfer linkage 60 moves during use. Thus, in one aspect the motor can cycle the power transfer linkage at a frequency greater than 100 Hz and the power transfer linkage can flex the flexible seal at a frequency greater than 100 Hz. In another aspect, the power transfer linkage flexes the flexible seal at a frequency of approximately 200 Hz.

Figure 2:
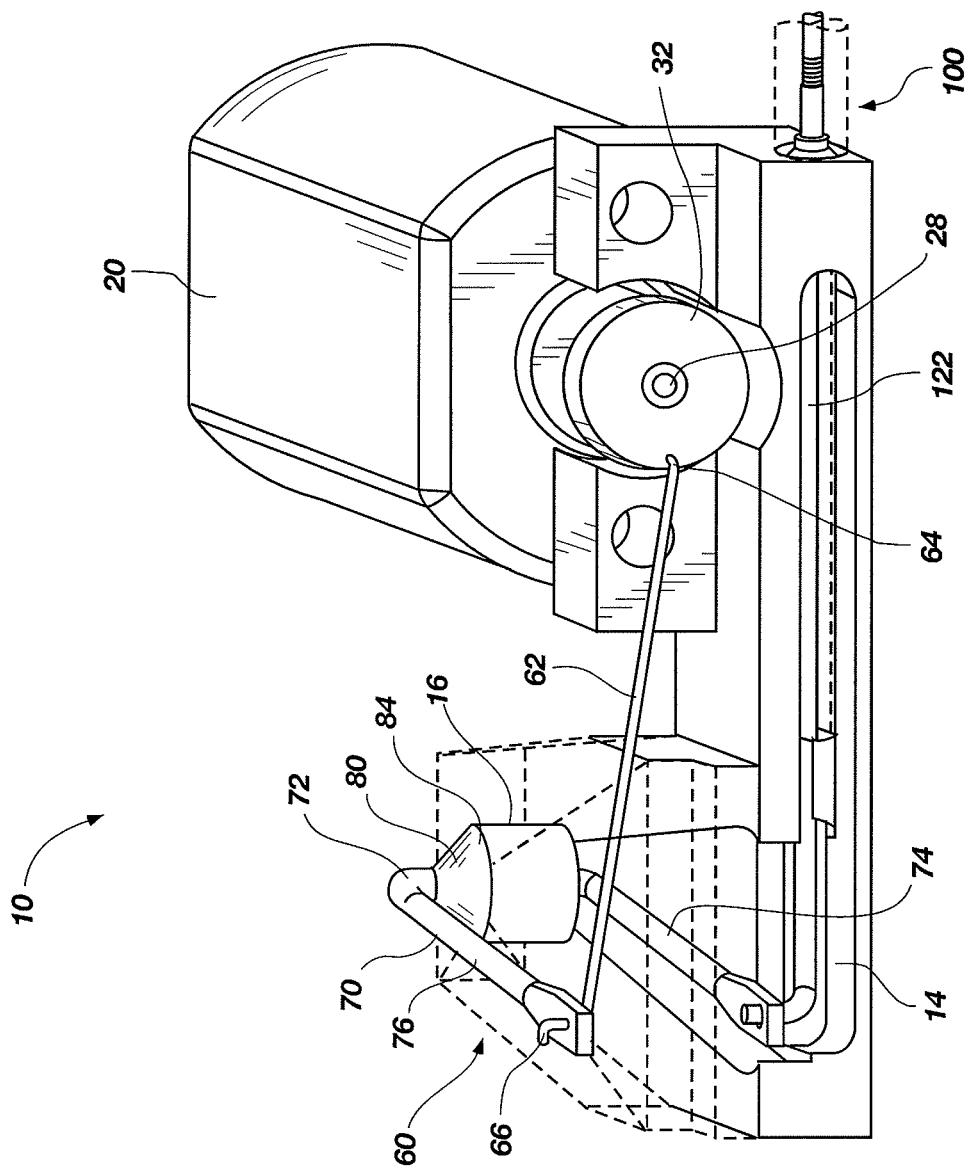
FIG. 2 is a schematic view of the miniature pump device of FIG. 1, showing an internal view of a fluid reservoir.
Figure 3:
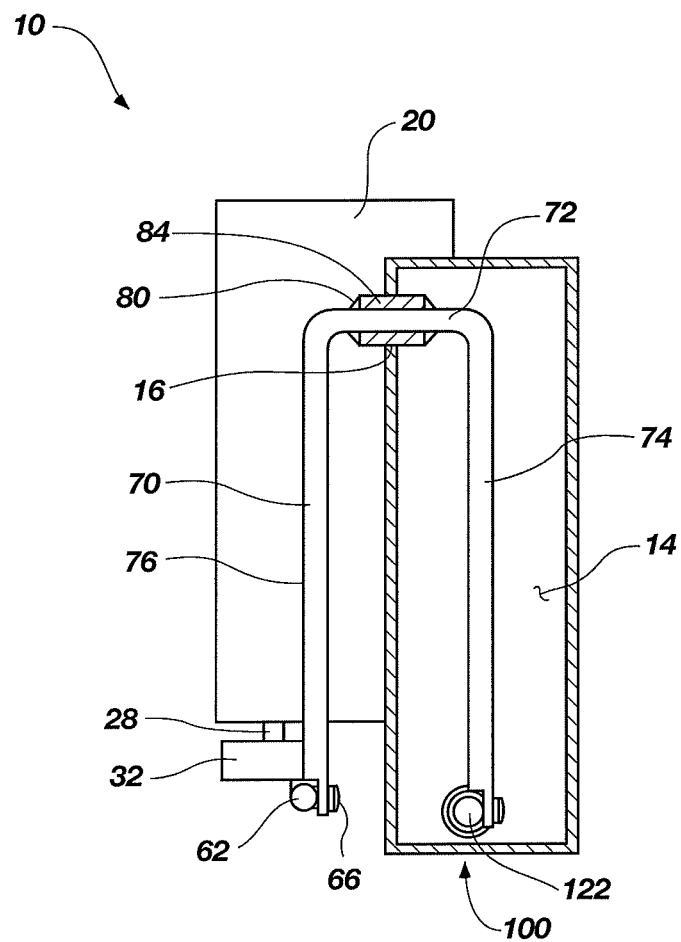
FIG. 3 is cross-sectional view of the miniature pump device of FIG. 1.
Figure 4:
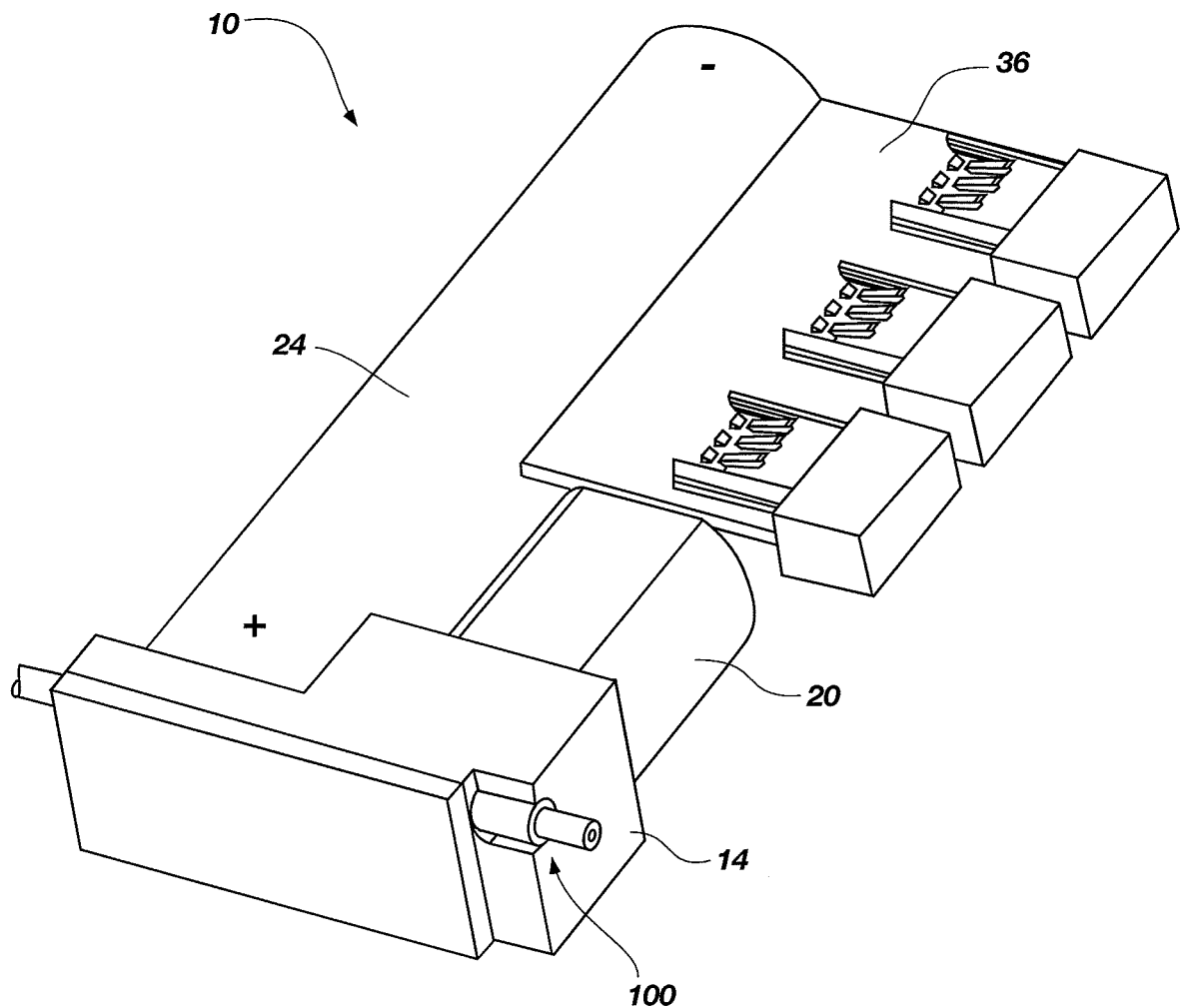
FIG. 4 is a perspective view of the miniature pump device of FIG. 1, shown with a power source and a controller.

As shown in FIGS. 1-3, the elastomeric plug 84 of the flexible seal 80 can be bonded to the base 72 of the U-shaped linkage 70 so that the outside arm 76 is outside the fluid reservoir 14 and the reservoir arm 74 is inside the fluid reservoir 14, with the flexible seal 80 disposed between these, sealing the fluid reservoir. The elastomeric plug 84 and U-shaped linkage 70 can be placed in an aperture 16 in a wall of the housing defining the fluid reservoir 14 so as to extend from outside the fluid reservoir to inside of the fluid reservoir, with the elastomeric plug 84 sealing against the reservoir arm 74 inside the fluid reservoir 14.

In use, the elastomeric plug 84 can rotationally stretch or flex with the base 72 of the U-shaped linkage 70 as the U-shaped linkage 70 pivots about the base 72 without breaking the seal around the base 72 or the fluid reservoir 14. Additionally, the elastomeric plug 84 can stretch or flex elastically so that the plug 84 can return to an un-flexed position when not in use. Advantageously, rotationally stretching and flexing the flexible seal 80 instead of linearly sliding or moving a seal requires less energy to actuate the piston 100 and, thus, the pump 10 can employ a smaller power source 24 in order to pump fluid. Rotationally stretching and flexing the flexible seal further allows the elastomeric plug to remain in a static plane about the housing of the pump, or rather to be in continuous contact with the wall structure of the housing. As the motor is operated and the pump actuated, the flexible seal (elastomeric plug 84) remains seated, with the only substantial movement being in a rotational direction rather than in a linear direction. There may be some small amount of linear movement, but this is negligible. Thus, the flexible seal 80, including the elastomeric plug 84, is an example of one means for flexibly sealing (and specifically rotationally flexibly sealing) a portion of the power transfer linkage 60 in the fluid reservoir 14 to restrict fluid from escaping from fluid reservoir 14 as the power transfer linkage 60 moves during use.

Figure 5:
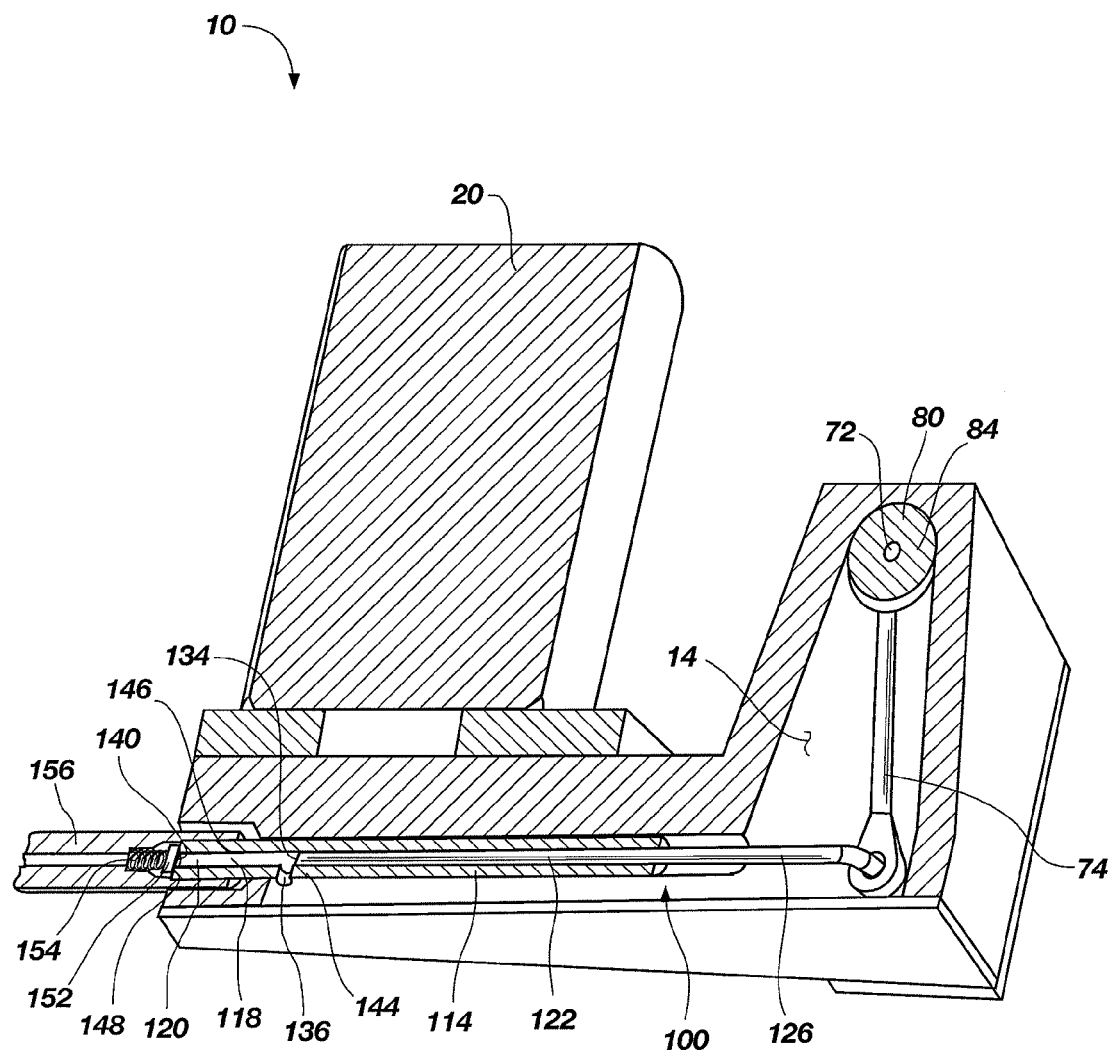
FIG. 5 is a perspective cut-away view of the miniature pump device of FIG. 1, shown with a piston in an open position.
Figure 6:
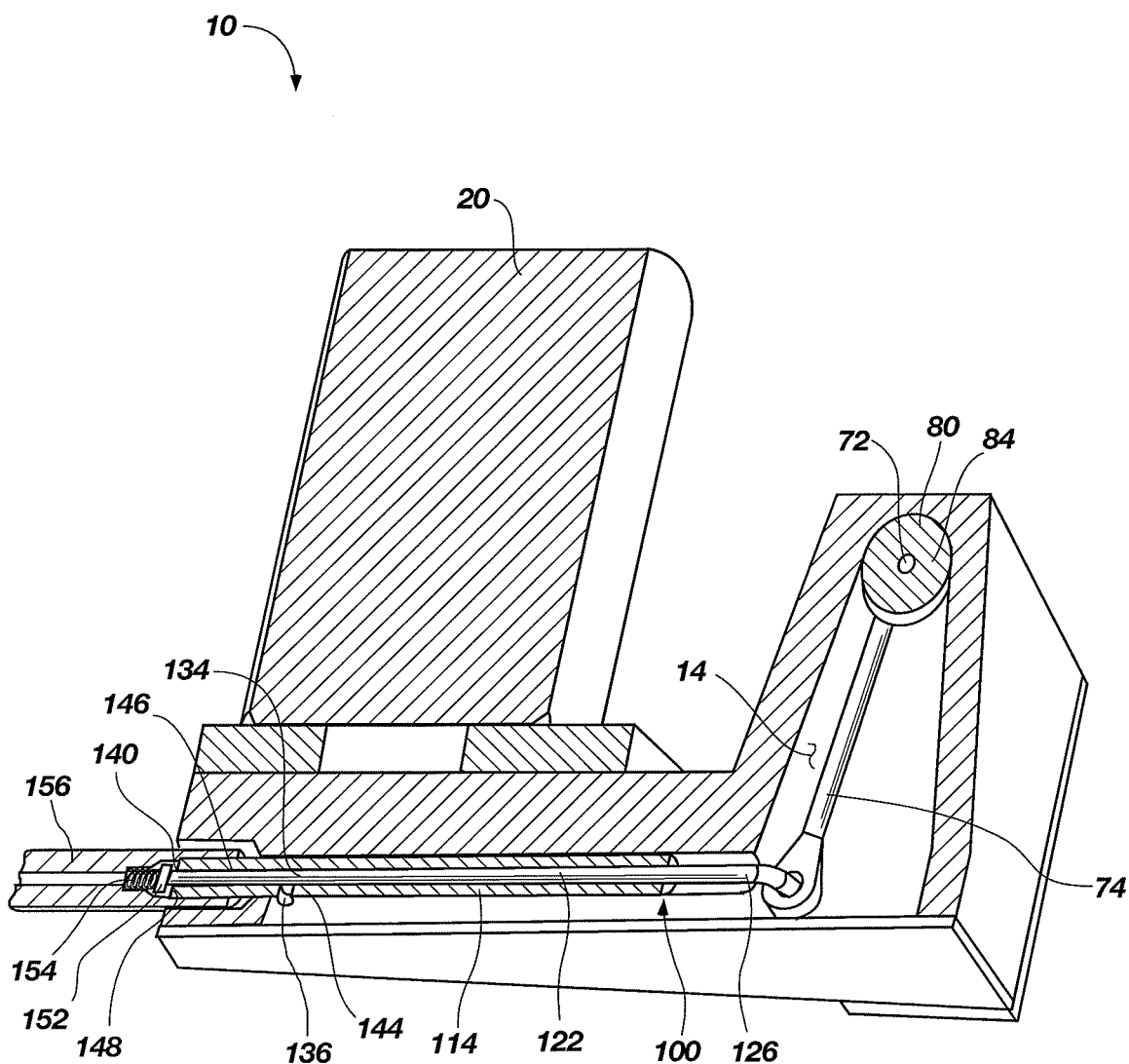
FIG. 6 is a perspective cut-away view of the miniature pump device of FIG. 5, shown with the piston in a closed position.

Referring to FIGS. 5-6, a cut away view of the miniature pump 10 is shown to better illustrate the piston 100. The piston 100 can be entirely disposed in the fluid reservoir 14, and can draw fluid from the fluid reservoir 14 and expel the drawn fluid from the fluid reservoir 14 and the pump. The piston can comprise a hollow cylinder 114 that has a fluid chamber 118 forming a fluid flow path 120 between an inlet 136 that is in fluid communication with the fluid reservoir 14 and an outlet 140 in the top 148 of the hollow cylinder 114.

A piston rod 122 can be slidably disposed in the hollow cylinder 114, and can be slidable between an open position, as shown in FIG. 5, and a closed position, as shown in FIG. 6. The piston rod 122 can be sized and shaped to have a near interference fit with the fluid chamber 118 of the hollow cylinder 114. The piston rod 122 can extend from within the chamber 118 to an end 126 in the fluid reservoir 14. The end in the fluid reservoir 14 can be pivotally coupled to the reservoir arm 74 of the U-shaped linkage 70 so that as the reservoir arm 74 moves back and forth, the piston rod 122 is moved between the open and closed positions. In one aspect, movement of the piston rod 122 to the open position can create a vacuum in the chamber 118, and the vacuum can draw fluid from the fluid reservoir 14 into the chamber 118.

The piston rod 122 can be precisely sized to form a slidable fluidic seal with the chamber 118 so that fluid cannot escape the chamber 118 by moving past the piston rod 122. The piston rod 122 can also have a substantially flat face 134 that can be substantially orthogonal to the side wall 146 of the chamber 118. It will be appreciated that the substantially orthogonal interface between the flat face of the piston rod 122 and the chamber 118 can reduce stagnation and cavitation of the fluid as it enters and moves through the chamber 118. Specifically, the flat face 134 can push the entire volume of the chamber 118 as the piston rod 122 moves during use.

The fluid inlet 136 can be a hole or aperture in a side wall 144 of the cylinder 114 that extends through the side wall 144 to the chamber 118. The outlet 140 can be a hole at the top 148 of the cylinder 114. The cylinder 114 can be disposed in the fluid reservoir 14 so that when the piston rod 122 is in the open position, fluid from the fluid reservoir 14 can flow into the chamber 118 through the inlet 136.

A valve 152 can be disposed across the top 148 of the cylinder 114 and can be biased to close off the top 148 of the cylinder 114 and the outlet 140. In one aspect, the valve 152 can be biased by a spring 154 to maintain the valve 152 in a closed position. In another aspect, or in combination with a spring, backflow pressure from fluid in an outlet fluid line 156 can bias the valve 152 to a closed position. The valve 152 can be opened by force from within the chamber 118 to allow fluid to exit through the outlet 140. The top 148 of the cylinder 114 can be coupled to the outlet fluid line 156. The outlet fluid line 156 can deliver the fluid to a desired location. The valve 152 can be entirely disposed within the outlet fluid line 156. In one aspect, the valve 152 can be a gate valve, as shown in FIGS. 5-6, wherein the gate is biased towards and linearly seated against the top 148 of the cylinder 114. In another aspect, the valve can be a ball valve. It will be appreciated that different types of valves can be used to close the chamber 118.

In use, the piston 100 can turbulently draw fluid from the fluid reservoir 14 into the fluid chamber 118 of the cylinder 114 through the inlet 136 when the rod 122 is positioned in the open position. Advantageously, the turbulence of the fluid entering the chamber 118 can displace any gaseous bubbles within the chamber 118. The piston rod 122 can then expel the contents of the fluid chamber 118 through the outlet 140 by being slid to the closed position. Sliding the piston rod 122 to the closed position pushes the fluid contained within the chamber 118 toward the outlet 140 and the valve 152. The fluid being pushed by the piston rod 122 can force the valve open so the fluid can exit the chamber 118 and enter the outlet fluid line 156. As the piston is being moved closer towards the closed position, the piston rod 122 can contact and force open the valve 152 so that the entire volume of the chamber 118 can be filled with the piston rod 122, thereby leaving no empty space in the chamber 118 in which stagnant bubbles can remain. Thus, the piston rod 122 and the hollow cylinder 114 together can form a piston 100 that can expel gas bubbles from the fluid chamber 118 of the hollow cylinder 114. A piston 100, including a flat face piston rod 122 slidably disposed within a hollow cylinder 114, is an example of one means for expelling gas bubbles from the piston 100.

In one aspect, the piston rod 122 and the cylinder 114 can be made from a glass material in order to provide a low friction interface between the piston rod 122 and the chamber 118 in the cylinder 114. Advantageously, the low friction interface between the piston rod 122 and the chamber 118 requires only small amounts of energy to move the piston rod 122 in the chamber 118. Thus, the pump 10 of the present invention only needs a small power source (e.g., power source 24 shown in FIG. 4) to actuate the piston 100.

The design of the piston 100 provides several advantages to the miniature pump 10. For example, as noted above, the flat face 134 and precision fit of the piston rod 122 against the cylinder 114 operate to push the entire volume of fluid drawn into the chamber 118 out of the chamber 118 when the piston 100 moves during use. It will be appreciated that bubbles can form from cavitation or turbulence of fluid flow into and out of the chamber 118. Moreover, bubbles can become stuck in the chamber 118 by wicking or other capillary forces. These stagnant bubbles can fill a portion of the volume of the chamber 118 and therefore decrease the output volume of the pump 10. Advantageously, the flat face 134 and precision fit of the piston rod 122 within the cylinder 114 forces a complete evacuation of the contents of the chamber 118, thereby leaving no space within the chamber 118 for excess fluid or bubbles to accumulate and remain. Hence, the design and fit of piston 100 in the pump 10 of the present invention can maximize the flow rate of the pump 10.

Additionally, it is a particular advantage of the miniature pump of the present invention that a small power source can be used to power the motor and the piston. It will be appreciated that a large power source or battery makes placement of a pump in small and confined spaces extremely difficult, if not impossible in many cases. For example, a miniature pump used as sub-dermal drug delivery device cannot be disposed below the skin in the abdominal cavity of a patient if the pump requires a battery larger than the space within the abdominal cavity in order to operate. Furthermore, multiple batteries and their eventual replacement can be a complex task in the small spaces such a miniature pump is likely to be used. Consequently, the stationary flexible seal and the low friction interface of the piston allow the miniature pump of the present invention to operate with much smaller power sources than other pumps of similar volumetric output. Thus, in one aspect, it has been discovered that the miniature pump device of the present invention utilizes only approximately ¼ the power needed by other pumps of similar volumetric output, and can be powered using a relatively small power source, such as, for example, a single AAA size battery.

Figure 7:
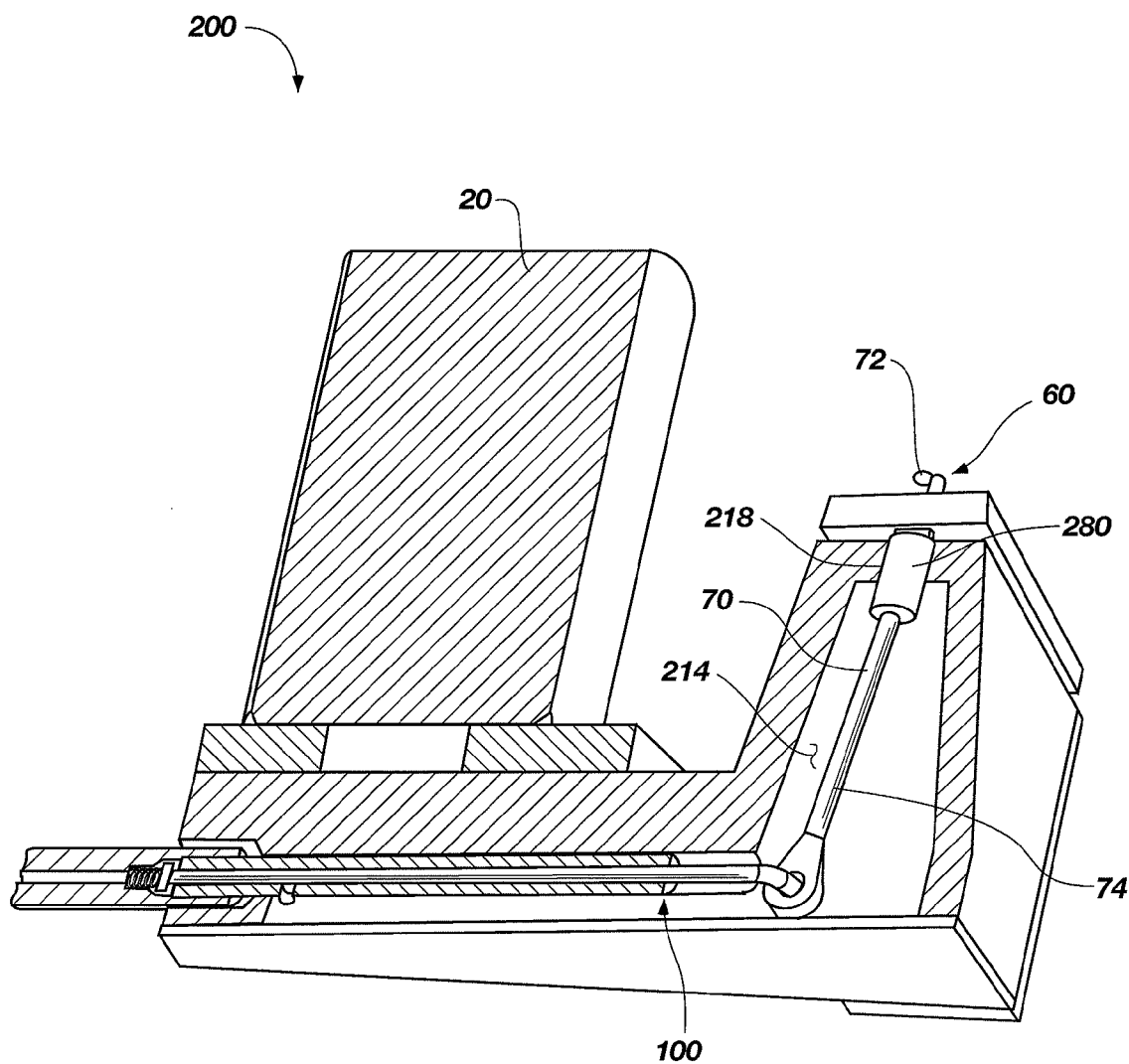
FIG. 7 is a perspective cut-away view of a miniature pump device in accordance with another exemplary embodiment of the present invention, shown with a piston in a closed position.
Figure 8:
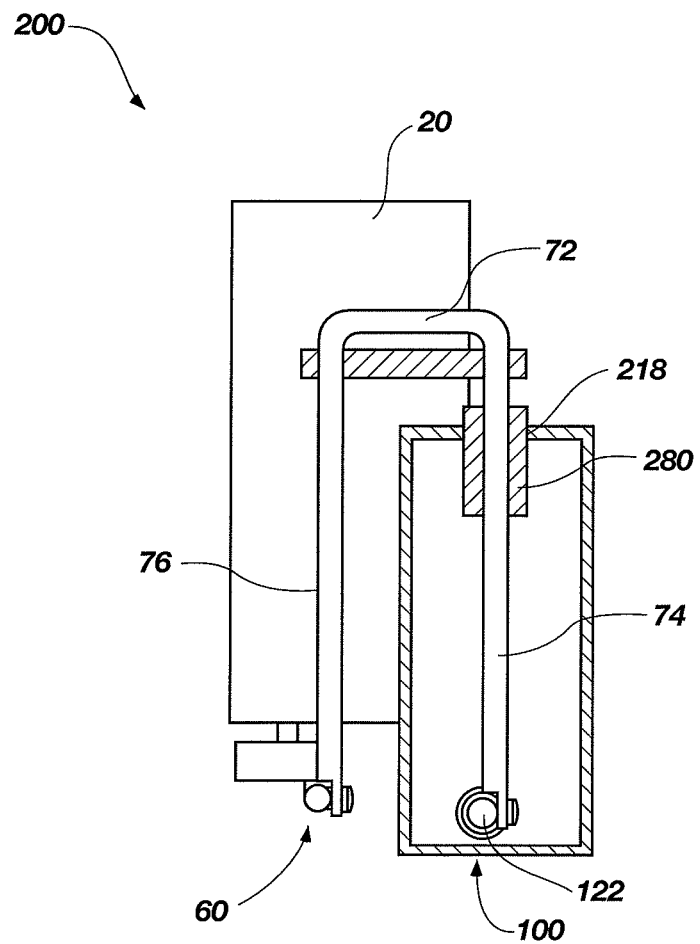
FIG. 8 is a cross-sectional view of the miniature pump of FIG. 7.

As illustrated in FIGS. 7-8, a miniature pump device, shown generally at 200, is shown in accordance with another exemplary embodiment of the present invention. The miniature pump 200 is similar in many respects to the miniature pump device 10 described above and illustrated in FIGS. 1-6, but is comprises a different type and functioning seal. As with the embodiment discussed above, the miniature pump device 200 can have a fluid reservoir 214 that can contain an intravenous drug, hydraulic fluid, or the like. The pump 200 can also have a motor 20 disposed adjacent the fluid reservoir 214, and a piston 100 disposed within the fluid reservoir 214. A power transfer linkage, shown generally at 60, can transfer power from the motor 20 to the piston 100 in the fluid reservoir 214, and a stationary flexible seal 280 can be coupled between the fluid reservoir 214 and the power transfer linkage 60 to seal a portion of the power transfer linkage 60 within the fluid reservoir 214. Thus, as discussed above, fluid leakage can be restricted by the flexible seal 280 as the motor 20 drives the power transfer linkage 60.

The power transfer linkage 60 can include a U-shaped linkage 70 that can have an outside arm 76, a base 72, and a reservoir arm 74. The reservoir arm 74 can extend at least partially into the fluid reservoir 214. In this particular embodiment, the flexible seal 280 comprises a linearly flexing seal. The flexible seal 280 can be bonded to the reservoir arm 74 and can fit within an aperture 218 in the fluid reservoir 214. The flexible seal 280 can seal around the aperture 218 in the fluid reservoir 214 to restrict fluid leakage from the reservoir 214. The flexible seal 280 can elastically flex as the reservoir arm 74 of the U-shaped linkage 70 moves in the aperture 218. It will be appreciated that the flexible seal 280 flexes linearly away from or towards the reservoir arm 74, as opposed to the rotational flexing of the flexible seal 80 that is bonded to the base 72 of the U-shaped linkage 60 shown in FIGS. 1-6, and described above. The pump 200 can be configured with many similar components and can function in most respects like the pump 10 discussed above.

Figure 9:
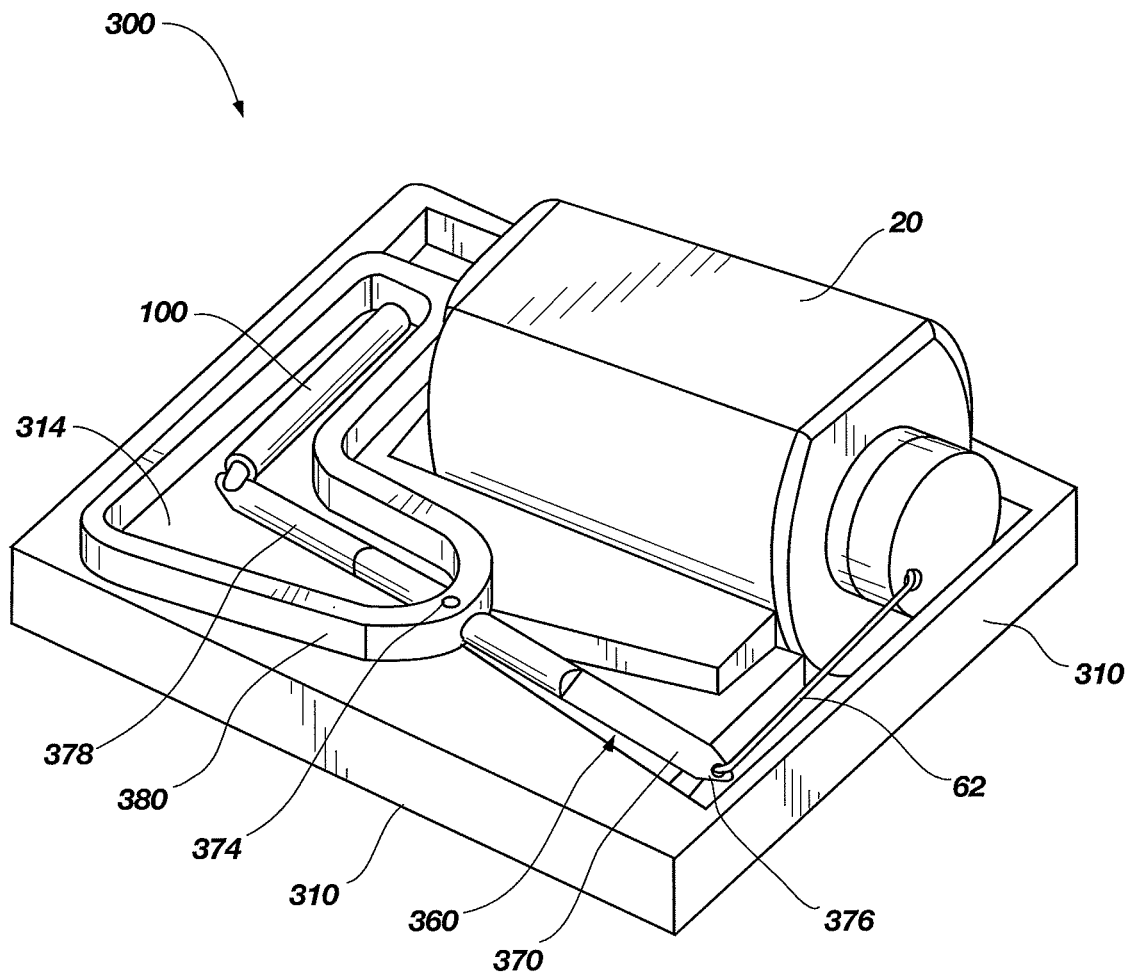
FIG. 9 is a perspective view of a miniature pump device in accordance with another embodiment of the present invention.

With reference to FIG. 9, a miniature pump device, provided generally at 300, is shown in accordance with another exemplary embodiment of the present invention. The miniature pump 300 is similar in many respects to the miniature pump device 10 described above. The miniature pump device 300 can have a fluid reservoir 314 that can contain an intravenous drug, hydraulic fluid, or the like. The pump 300 can also have a motor 20 disposed adjacent the fluid reservoir 314, and a piston 100 disposed within the fluid reservoir 314. A power transfer linkage, shown generally at 360, can transfer power from the motor 20 to the piston 100 in the fluid reservoir 314, and a stationary flexible seal 380 can be coupled between the fluid reservoir 314 and the power transfer linkage 360 to seal a portion of the power transfer linkage 360 within the fluid reservoir 314. Thus, fluid leakage can be restricted by the flexible seal 380 as the motor 20 drives the power transfer linkage 360.

Different from the other embodiments discussed above, the power transfer linkage 360 can include a flexible linkage 62 coupled to an end 376 of a linear rocker arm 370. The linear rocker arm 370 can extend at least partially into the fluid reservoir 314. The linear rocker arm 370 can be pinned to a pump housing 310 by a pivot pin 374 allowing the rocker arm to pivot or rock about a pivot point formed by pivot pin 374. An opposite end 378 of the linear rocker arm can be coupled to the piston 100. Thus, in use, the motor can move the flexible linkage 62 which can pivot the linear rocker arm 370 about the pivot pin 374, thereby moving the piston to pump fluid from the fluid reservoir 314.

The flexible seal 380 can be bonded to the linear rocker arm 370 and can extend from the linear rocker arm entirely around a circumference of the fluid reservoir 314. In this way the flexible seal can seal around the linear rocker arm 370 and also around the entire fluid reservoir 314 to restrict fluid leakage from the reservoir 314. The flexible seal 380 can elastically flex as the linear rocker arm 370 rocks about the pivot pin 374. It will be appreciated that a portion of the flexible seal 380 stretches on one side of the rocker arm 370 and a portion compresses or mashes on an opposite side of the rocker arm, as opposed to the rotational or linear flexing of the flexible seals shown in FIGS. 1-8, and described above.

The present invention also provides for a method for expelling gas bubbles from a miniature pump device including providing a miniature pump having a piston disposed in a fluid reservoir. The piston can have a hollow cylinder and a rod slidably disposed in the hollow cylinder. The rod can be sized and shaped to have a near interference fit within the hollow cylinder. The rod can be slid within the hollow cylinder past an inlet to an open position to draw fluid from the fluid reservoir through the inlet and into a chamber within the hollow cylinder. The creation of any turbulence of the fluid entering the chamber can help to displace any gaseous bubbles within the chamber. The rod can be slid to a closed position with the rod closing the inlet and pushing the contents of the chamber through an outlet of the hollow cylinder.

The present invention can also include a unidirectional anti-free flow valve. The valve can allow flow from an inlet to an outlet and can function to restrict flow through the valve except when the miniature pump described above is operating. In this way the anti-free flow valve can restrict flow through the valve when a pressure is applied to the fluid reservoir and also when a negative pressure is applied at the outlet (such as when the piston is being positioned from a closed position to an open position). Thus, the pump device of the present invention provides particular advantages to certain medical applications. For example, the pump is particularly suited for use as an intravenous drug delivery pump because the anti-free flow valve restricts inadvertent drug delivery through the pump if the drug reservoir is pressurized, such as by squeezing an IV bag. Additionally, inadvertent drug delivery is restricted if a negative pressure is experienced at the pump outlet.

In the embodiments described herein, the anti-free flow valve can be a miniature unidirectional valve configured to restrict the free flow of fluid through the valve. The valve can include a valve body having an inlet and an outlet. A valve gate can be disposed in the valve body. The valve gate can be operable between an open position defining an unobstructed fluid flow path between the inlet and outlet, and a closed position obstructing the outlet to restrict fluid flow therethrough. A fluid reservoir can be in fluid communication with the valve gate such that pressure from the fluid reservoir can operate to urge the valve gate towards the closed position. A biasing device can be associated with the valve gate to bias the valve gate to the closed position to restrict fluid flow therethrough. Additionally, a pressure from the inlet can operate on the valve gate to overcome the pressure from the fluid reservoir and the biasing device, thereby opening the valve gate.

In one aspect, as shown in FIGS. 10-13, the valve gate can be a flexible and stretchable membrane that is movably disposed over the inlet and outlet. The membrane can move between an open position and a closed position. Pressure from a fluid reservoir can be utilized to urge the flexible membrane to the closed position. A biasing device, such as a preload structure can stretch the flexible membrane against the outlet to close the outlet and restrict fluid flow therethrough. The flexible membrane can be moved by a pressure from the inlet to move the membrane to the open position. Thus, the pressure from the reservoir can restrict opening of the valve gate or flexible membrane in the event a positive pressure is realized in the outlet, and the force of the biasing member or preload structure can maintain the flexible membrane in the closed position in the event of a drop in pressure in the reservoir. Thus, the flexible membrane is one example of a valve gate of the present invention.

Figure 10:
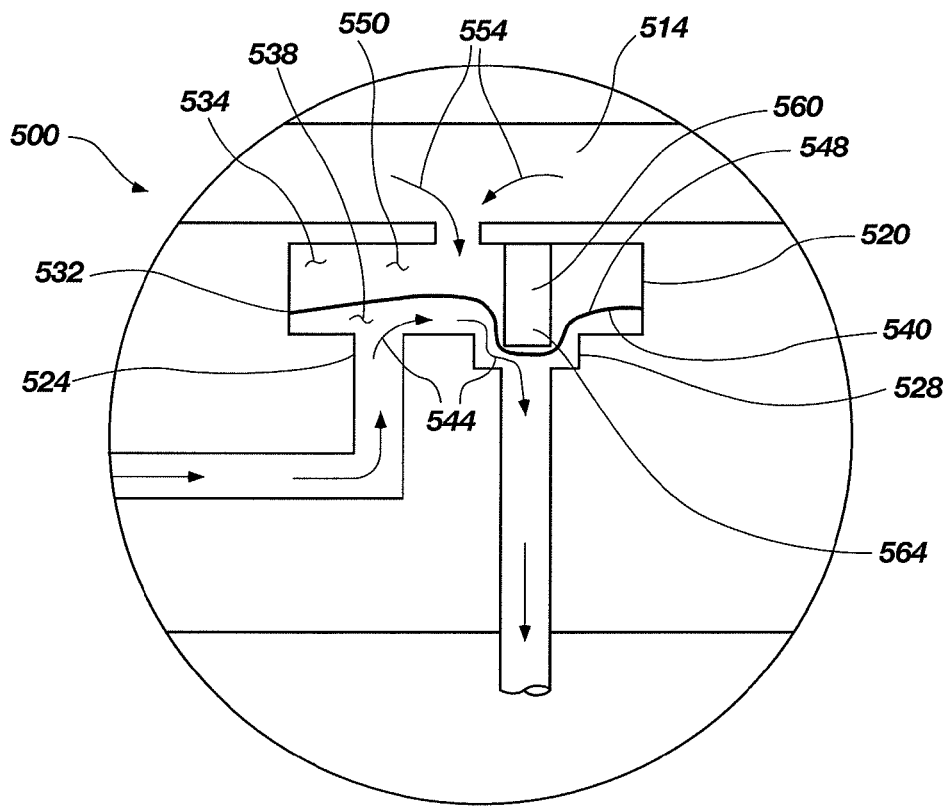
FIG. 10 is a schematic view of an anti-free flow valve in accordance with another exemplary embodiment of the present invention, shown with the valve in an open configuration.
Figure 11:
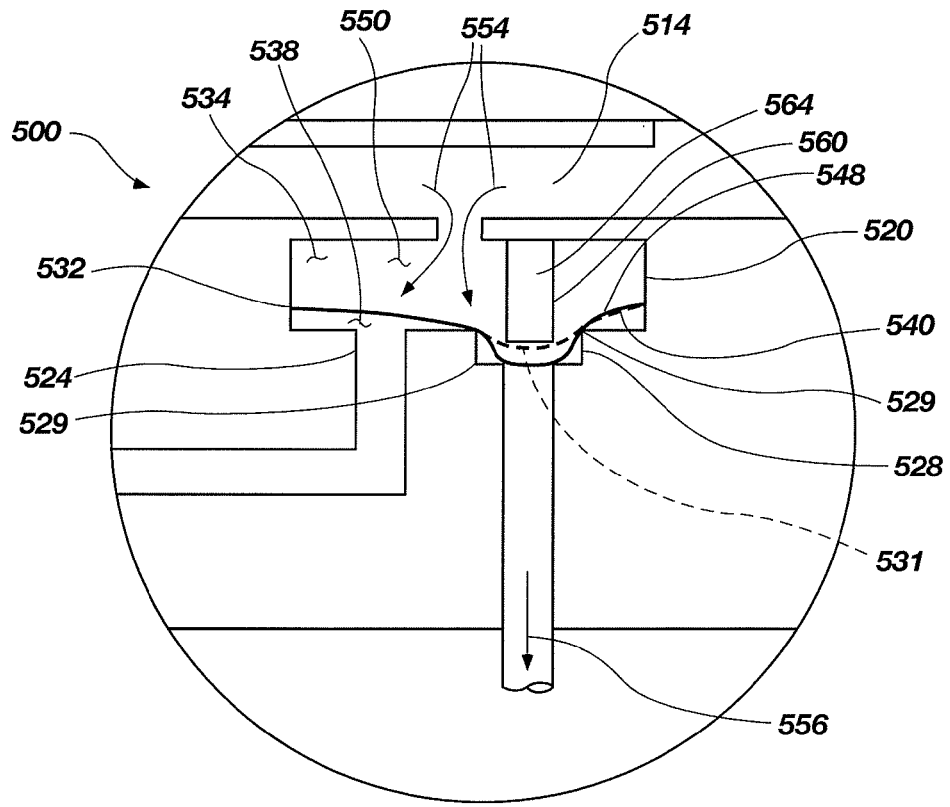
FIG. 11 is a schematic view of the anti-free flow valve of FIG. 10, shown with the valve in an closed configuration.

Accordingly, as illustrated in FIGS. 10-11, a unidirectional valve, indicated generally at 500, is shown in accordance with another exemplary embodiment of the present invention for use in restricting the free flow of fluid through the valve 500. The valve 500 can have a valve body 520 that has an inlet 524 and an outlet 528.

The valve 500 can also have a stretchable and flexible membrane 540. The stretchable flexible membrane 540 can be movably disposed over the inlet 524 and outlet 528. The stretchable flexible membrane 540 can move between an open position, as shown in FIG. 10, and a closed position, as shown in FIG. 11. In the open position, the membrane 540 can define an unobstructed fluid flow path, indicated by arrows at 544, between the inlet 524 and outlet 528. In the closed position, the stretchable flexible membrane 540 can seal the outlet 528 to restrict fluid flow through the outlet.

The stretchable flexible membrane 540 can be disposed across the valve body 520 and can separate the valve body to define a control chamber 550 and the fluid flow path 544. In one aspect, the control chamber can be adjacent the fluid flow path. For example, the membrane 540 can be an elastomeric sheet 548 that can be bonded to a periphery 532 of the valve body 520 to separate the valve body into a first portion 534 on a first side of the elastomeric sheet 548 and a second portion 538 on an opposite, second side of the elastomeric sheet. Thus, the control chamber 550 can be defined by the first portion 534 of the valve body 520 on the first side of the elastomeric sheet 548, and the fluid flow path 544 can be defined by the second portion 538 of the valve body on the opposite side of the elastomeric sheet 548 and adjacent the control chamber. Additionally, the elastomeric sheet 548 can seal around the valve body periphery 532 to restrict communication between the control chamber 550 and the fluid flow path 544.

The stretchable flexible membrane 540 can be moved to the open position by force or pressure from fluid entering the inlet 524 that pushes the membrane away from the outlet 528 and allows fluid to travel through outlet along the fluid flow path 544. Additionally, the membrane 540 can be moved to the closed position by a force or pressure from either the control chamber 550 or the outlet 528.

Thus, in one aspect, the control chamber 550 can be in fluid communication with a fluid reservoir 514 and the fluid in the fluid reservoir 514 can apply a pressure, indicated by arrows at 554, against the flexible membrane 540 to move the membrane to the closed position against the outlet 528 to restrict fluid flow through the valve 500. Moreover, a negative pressure, or suction, indicated by the arrow at 556, applied about the outlet 528 can apply a force or pressure to the flexible membrane 540 to draw the membrane to the closed position against the outlet 528. Thus, the flexible membrane 540 can be moved to the closed position when the pressure from the fluid in the fluid reservoir 514 or suction in the outlet 528 exceeds the pressure from fluid in the inlet. Alternatively, the flexible membrane 540 can be moved to the open position when the pressure from fluid in the fluid inlet 528 exceeds the pressure from the fluid in the fluid reservoir 514.

The valve can also have a preload structure 560. The preload structure 560 can be disposed in the valve body 520 and associated with the flexible membrane 540. The preload structure 560 can bias the flexible membrane 540 toward the closed position to close the outlet 528. In this way, the preload structure 560 is one example of a biasing member that biases the valve gate to the closed position.

The preload structure can include a protrusion 564 in the control chamber 550 that can protrude into the outlet 528 and press the flexible membrane toward the outlet. In one aspect, the preload structure 560 can comprise a structural component or member extending from and supported by the valve body, or which can comprise an integral extension of the valve body itself. The protrusion can operate to stretch the flexible membrane and force the stretched membrane to contact and seal onto or against corners 529 of the outlet 528, as shown by the dashed line 531 representing the flexible membrane in the stretched position being stretched by the preload structure 560. In this way, the preload structure 560 ensures closure of the valve until the pressure in the inlet 524 exceeds the pressure in the control chamber 550.

Thus, in use, when the pressure in the inlet 524 is greater than the pressure in the control chamber, the membrane 540 is pushed away from the corners 529 of the outlet 528 and the fluid can flow from the inlet 524 past the membrane and outlet 528. Additionally, under conditions when the pump is not operating, the pressure from the reservoir 514 can push the membrane 540 against the outlet 528 to seal the valve and the preload structure 560 can stretch the membrane 540 to force the membrane, as shown by dashed line at 531, against the corners 529 to ensure sealing of the membrane against fluid flow. Moreover, a negative pressure from the outlet 528 will draw the membrane, as shown by solid line 540, against the outlet 528 to keep the valve closed. Thus, the anti-free flow valve 500 described in the embodiments herein can prevent flow through the valve 500 if the pressure in the control chamber 550 is increased and also if a sucking, siphoning, or negative pressure is applied about the outlet 528.

In this way, a pressure drop between the control chamber side of the membrane and the flow path, or inlet and outlet side of the membrane will, advantageously, always favor the closing of the membrane, and hence closing of the valve. Thus, advantageously, the valve 500 restricts flow in the event of increased pressure on the reservoir 514, such as if the reservoir 514 included a flexible bag (not shown) that was squeezed inadvertently, and also the valve 500 can restrict flow if an undesirable siphoning force is applied to the outlet 528.

Figure 12:
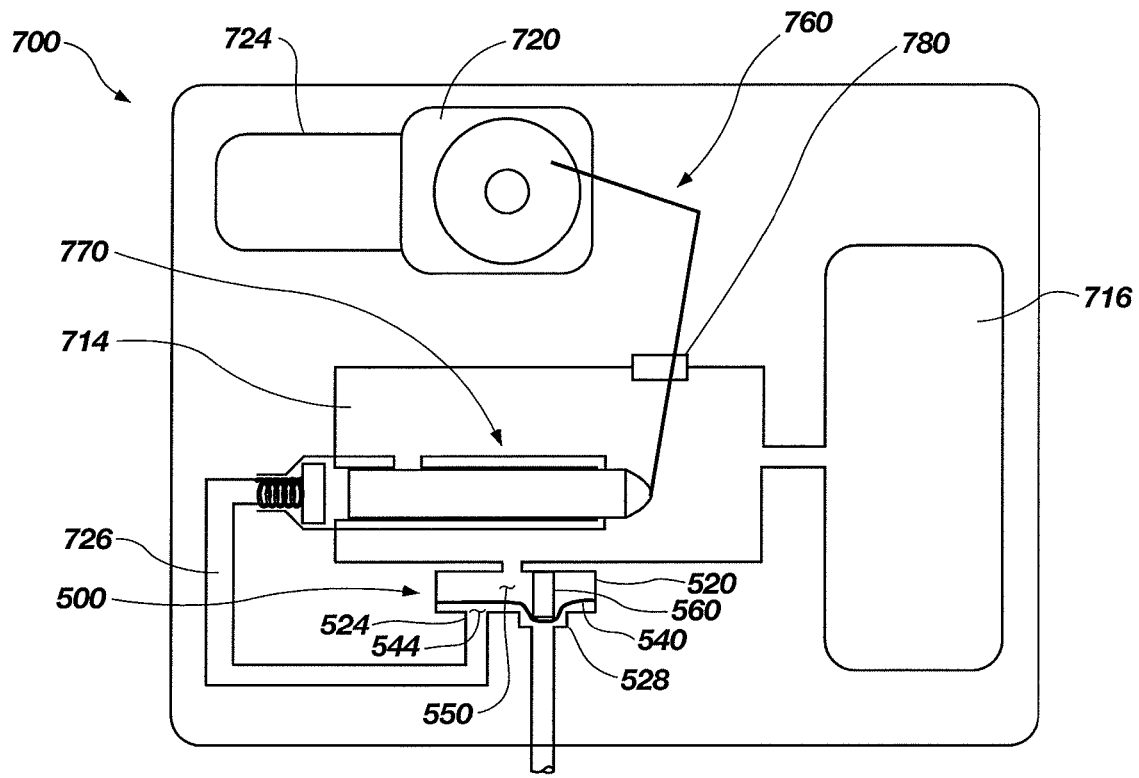
FIG. 12 is a schematic view of a miniature pump device coupled to the anti-free flow valve of FIG. 10, shown with the valve in an open configuration.
Figure 13:
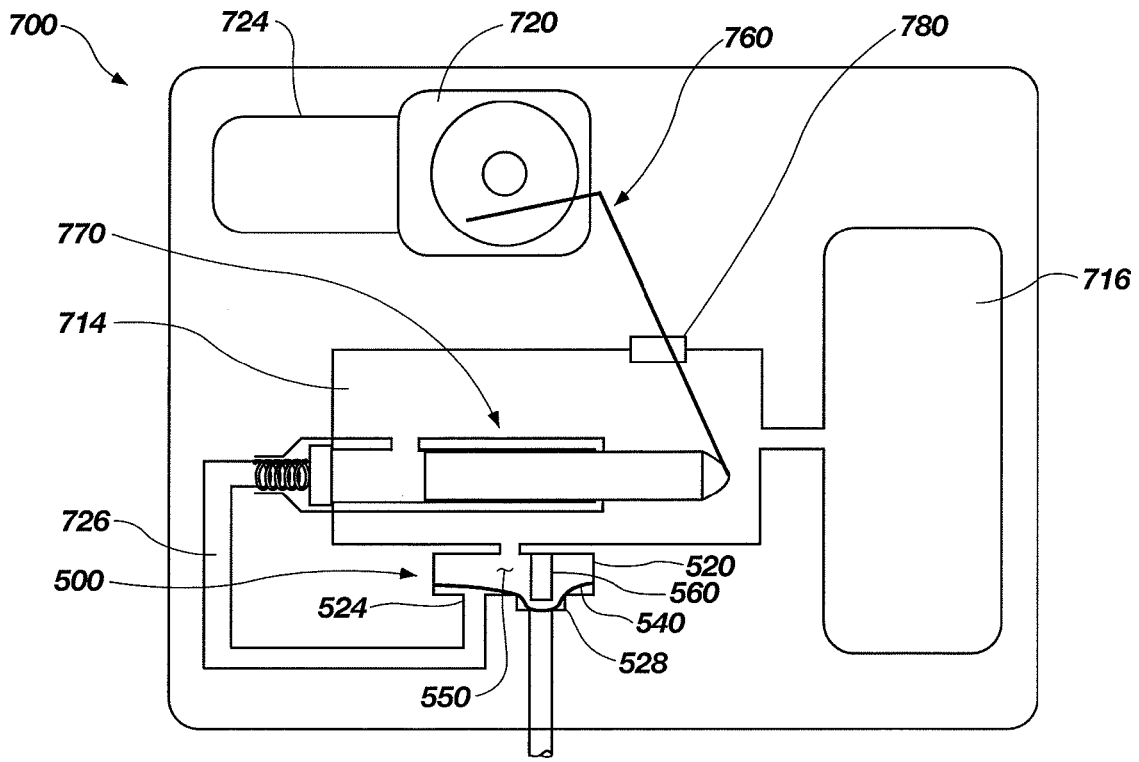
FIG. 13 is a schematic view of the miniature pump of FIG. 12, shown with the valve in a closed configuration.

As illustrated in FIGS. 12-13, the anti-free flow valve just discussed, indicated generally at 500 can be coupled to or otherwise caused to be operable with any or all of the miniature pump devices 10, 200, and 300 described above and illustrated in FIGS. 1-9. Thus, the present invention can provide a miniature pump device with an anti-free flow valve, indicated generally at 700 in accordance with an exemplary embodiment of the present invention.

The miniature pump device 700 can be similar in many respects to the pump devices described above and illustrated in FIGS. 1-9. Additionally, the miniature pump device 700 can include a fluid reservoir 714, a motor 720, a piston, indicated generally at 770, a power transfer linkage, indicated generally at 760, a flexible seal 780, and an anti-free flow valve 500.

The motor 720 can be electrically coupled to a power source 724, and disposed adjacent the fluid reservoir 714. The piston can be disposed in the fluid reservoir 714 and can draw and expel fluid from the fluid reservoir.

The power transfer linkage 760 can be coupled between the piston 770 and the motor 720. The power transfer linkage 760 can be partially disposed in the fluid reservoir 714, and can transfer power from the motor 720 to the piston 770 to drive the piston 770.

The flexible seal 780 can be coupled between the fluid reservoir 714 and the power transfer linkage 760. The flexible seal 780 can seal a portion of the power transfer linkage 760 in the fluid reservoir 714 and restrict fluid from escaping from fluid reservoir as the power transfer linkage moves during use.

The anti-free flow valve 500 can be operable to receive fluid expelled by the piston 770 via an inlet tube 726 that is in fluid communication with the piston. The valve 500 can restrict fluid from reentering the piston 770 or from flowing through the valve 500 without active operation of the piston. The valve 500 can include a valve body 520 having an inlet 524 and an outlet 528.

A flexible membrane 540 can be movably disposed over the inlet 524 and outlet 528. The flexible membrane 540 can be movable to an open position with the membrane defining an unobstructed fluid flow path 544 between the inlet 524 and outlet 528, as shown in FIGS. 10 and 12. The flexible membrane 540 can also be movable to a closed position with the membrane sealing the outlet 528 to restrict fluid flow through the valve 500, as shown in FIG. 13. The flexible membrane 540 can be movable by a pressure from the inlet 524 to move the membrane to the open position.

A control chamber 550 can be disposed in the valve body 520 on the opposite side of the flexible membrane 540, and can be in fluid communication with the fluid reservoir 714 of the micro pump. The control chamber 550 can receive pressurized fluid from the fluid reservoir 714, which pressure can then be applied against the flexible membrane 540 to move the membrane to the closed position against the outlet 528 to restrict fluid flow through the valve 500.

A preload structure 560 can be associated with the flexible membrane 540. The preload structure 560 can bias the flexible membrane 540 toward the closed position to close the outlet 528 and restrict fluid flow through the valve 500.

In use, as the piston 770 pumps fluid from the fluid reservoir 714 into the fluid line 726, which is in fluid communication with inlet 524 of the anti-free flow valve 500, the fluid can move through the inlet 524 into the valve body 520. Once the fluid is in the valve body 520, the fluid can push the flexible membrane 540 into the control chamber 550 in order to open the fluid flow path 544 and allow fluid to flow through the valve 500. After entering the fluid flow path 544 and moving the flexible membrane 540 to the open position, the fluid can move out the outlet 528 and exit the pump device.

Additionally, when the piston 770 is not pumping fluid into the valve inlet 524, the fluid in the fluid reservoir 714 can push against the flexible membrane 540 and move the flexible membrane to the closed position. Moreover, if excessive pressure is applied to the fluid reservoir 714, or an auxiliary reservoir 716, such as by squeezing an intravenous fluid bag, the excessive pressure can be transferred through the fluid in the control chamber 550 to move and retain the flexible membrane 540 in the closed position. Furthermore, if an external negative pressure or suction is applied to the outlet 528 of the valve 500, the flexible membrane 540 can be drawn into the outlet 528 to close the outlet and prevent fluid from leaving the valve 500.

Figure 14:
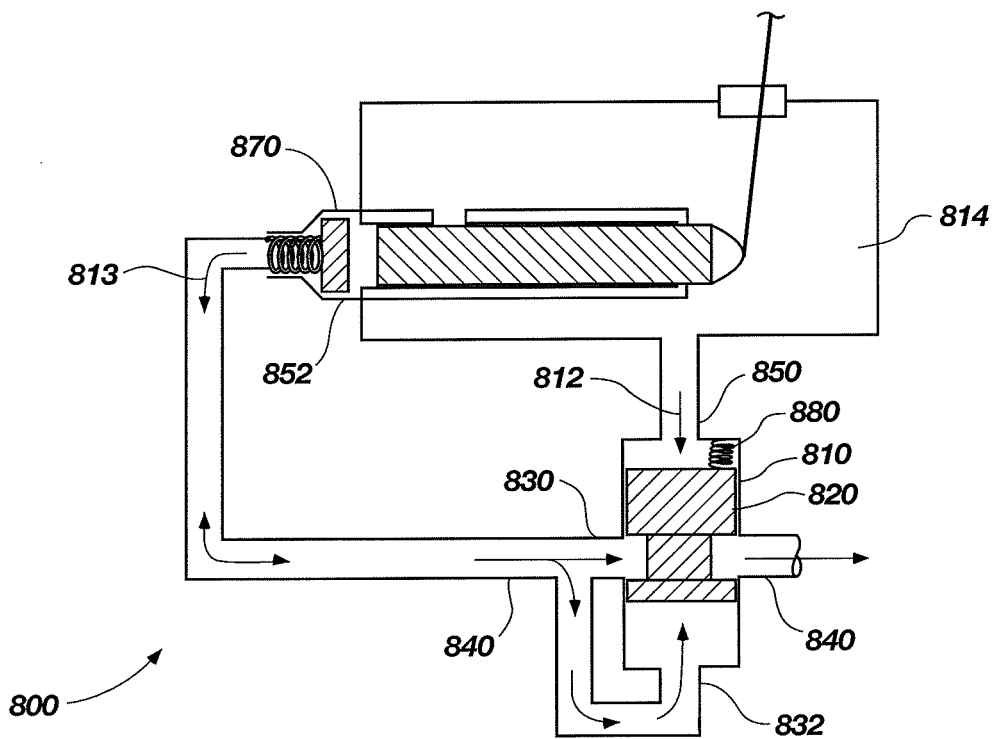
FIG. 14 is a schematic view of an anti-free flow valve in accordance with another exemplary embodiment of the present invention, with the valve shown in an open configuration.
Figure 15:
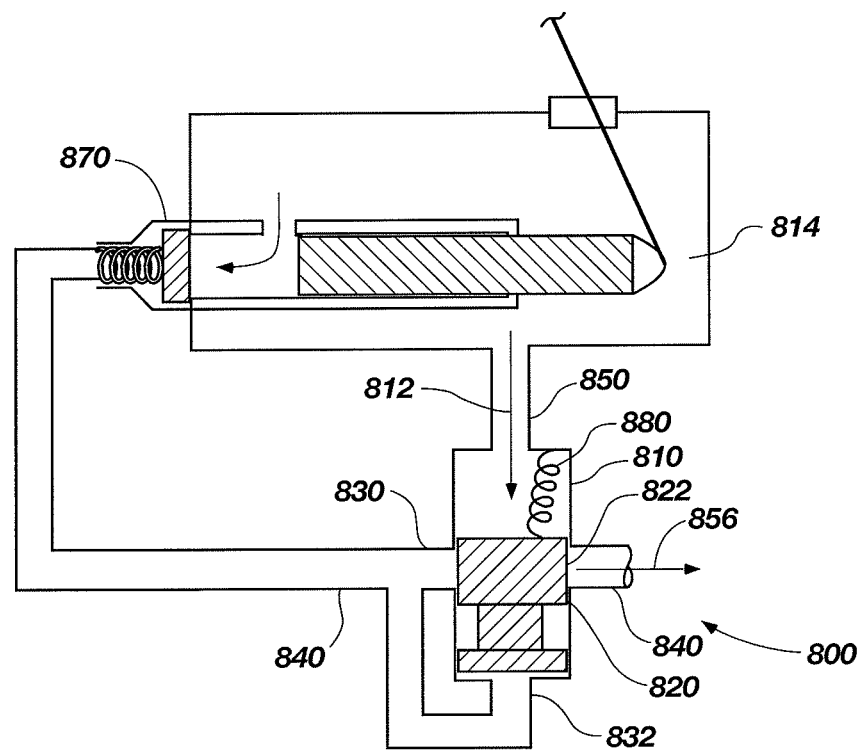
FIG. 15 is a schematic view of the anti-free flow valve of FIG. 14, shown in a closed configuration.

In another aspect, as shown in FIGS. 14-15, the valve gate can be a spool movably disposed over the inlet and outlet. Pressure from a fluid reservoir can be utilized to urge the spool to the closed position. A biasing device, such as a spring, can push the spool to close the outlet and restrict fluid flow therethrough. The spool can be moved by a pressure from the inlet to move the spool to the open position. Thus, the pressure from the reservoir can restrict opening of the valve gate or spool in the event a positive pressure is realized in the outlet, and the force of the biasing member or spring can maintain the spool in the closed position in the event of a drop in pressure in the reservoir. Thus, the spool is another example of a valve gate of the present invention.

As illustrated in FIGS. 14-15, a unidirectional valve, indicated generally at 800, is shown in accordance with an exemplary embodiment of the present invention for use in restricting the free flow of fluid through the valve 800 as this valve is operable with the pump. The valve 800 can be similar in many functional respects as the anti-free flow valve 500 described above and shown in FIGS. 10-11. Additionally, the anti-free flow valve 800 can be coupled to or otherwise operable with the miniature pump devices 10, 200, and 300 described above and illustrated in FIGS. 1-9.

The valve 800 can include a spool valve 810. The spool valve 810 can have a spool 820, an inlet 830 an outlet 840, and a biasing member 880. The biasing member 880 can bias the spool 820 to the closed position. In one aspect, the biasing member 880 can be a spring.

The inlet 830 can have a control line 832 that can allow pressure from the fluid flowing to the inlet to push the spool 820 to an open position so that the fluid can flow through the valve. The spool valve 810 can also have a control inlet 850. The control inlet 850 can be in fluid communication with a fluid reservoir 814 of a pump similar to the ones described herein. The pressure, shown as arrows 812, from the fluid reservoir 814 can act on one side of the spool 820 to push the spool to close the inlet and outlet of the spool valve. Similarly, pressure, shown as arrow 813, from the pump outlet 852 can act on an opposite side of the spool to push the spool to open the inlet and outlet of the spool valve to allow fluid to flow through the valve. In this way, pressure in the reservoir can close the valve if the reservoir pressure is greater than pressure from the pump.

Moreover, a negative pressure, or suction, indicated by the arrow at 856, applied about the outlet 840 of the valve can apply a force or pressure to the spool side wall 822 which is perpendicular to the direction of movement of the spool in the spool valve so that the suction force or pressure cannot open the spool valve. Thus, the spool 820 can be moved to the closed position when the pressure from the fluid in the fluid reservoir 814 exceeds the pressure from fluid in the inlet and suction or negative pressure forces at the outlet cannot push the spool to an open position. Alternatively, the spool 820 can be moved to the open position when the pressure from fluid in the fluid inlet 830 exceeds the pressure from the fluid in the fluid reservoir 814.

The present invention also provides for a method for restricting the free flow of fluid in a fluid delivery system, such as an intravenous drug delivery system, a sub-dermal drug pump, or the like, including providing a valve body having an inlet, an outlet, and a flexible membrane disposed across the inlet and outlet. The flexible membrane can define a fluid flow path between the inlet and the outlet on one side of the flexible membrane, and a control chamber on an opposite side of the flexible membrane. The fluid flow path can be opened with pressure from the inlet to move the flexible membrane to an open position such that flexible membrane defines an unobstructed fluid flow path between the inlet and outlet to allow fluid to flow between the inlet and the outlet. The fluid flow path can be closed by a pressure against the flexible membrane to move the flexible membrane to a closed position such that the flexible membrane presses against and seals over the outlet to restrict fluid flow therethrough. The flexible membrane can be biased toward the closed position with a preload structure such that closing the fluid flow path requires less pressure than opening the fluid flow path.

The step of opening the fluid flow path can also include moving a fluid into the inlet, such as with a piston pump. Additionally, the step of closing the fluid flow path can include supplying pressure to the control chamber to press the flexible membrane against the outlet to restrict fluid flow through the valve. Moreover, the step of closing the fluid flow path can include supplying negative pressure to the outlet to draw the flexible membrane against the outlet.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A miniature pump device with an anti-free flow valve, comprising:
    a fluid reservoir;
    a motor, configured to electrically couple to a power source, and disposed adjacent the fluid reservoir;
    a piston, disposed in the fluid reservoir, and operable with the motor to draw and expel fluid from the fluid reservoir;
    a power transfer linkage, coupled between the piston and the motor, partially disposed in the fluid reservoir, and configured to transfer power from the motor to the piston;
    a flexible seal, coupled between the fluid reservoir and the power transfer linkage, configured to seal a portion of the power transfer linkage in the fluid reservoir and restrict fluid from escaping from the fluid reservoir as the power transfer linkage moves during use; and
    the anti-free flow valve operable to receive fluid as pumped by the piston, the anti-free flow valve operating to restrict fluid from reentering the piston, the anti-free flow valve further comprising:
        a valve body having an inlet and an outlet;
        a flexible membrane movably disposed over the inlet and outlet, and movable between an open position with the membrane defining an unobstructed fluid flow path between the inlet and outlet, and a closed position with the membrane sealing the outlet to restrict fluid flow therethrough;
        a control chamber disposed in the valve body adjacent the fluid flow path and separated from the fluid flow path by the flexible membrane, the control chamber being in fluid communication with the fluid reservoir, and configured to apply a pressure against the membrane to move the membrane to the closed position against the outlet to restrict fluid flow therethrough;
        the flexible membrane being movable by a pressure from the inlet to move the membrane to the open position to open the outlet and permit fluid flow.

2. A device in accordance with claim 1, further comprising a preload structure associated with the flexible membrane, and configured to bias the flexible membrane towards the outlet to close the outlet and restrict fluid flow therethrough, wherein the preload structure includes a protrusion in the control chamber configured to press the flexible membrane against the outlet.

3. A device in accordance with claim 2, wherein the preload structure operates to bias the flexible membrane into the outlet such that the flexible membrane closes the outlet in the presence of a negative pressure in the outlet.

4. A device in accordance with claim 1, wherein the control chamber is subject to pressure from fluid in the fluid reservoir.

5. A device in accordance with claim 4, wherein the flexible membrane operates to move to the closed position when the pressure from the fluid in the fluid reservoir exceeds the pressure from fluid in the inlet.

6. A device in accordance with claim 4, wherein the flexible membrane operates to move to the open position when the pressure from fluid in the fluid inlet exceeds the pressure from the fluid in the fluid reservoir.

7. A device in accordance with claim 1, wherein the flexible membrane further comprises an elastomeric sheet disposed within the valve body to form the control chamber in a first portion of the valve body on a first side of the elastomeric sheet and the fluid flow path in a second portion of the valve body on a second side of the elastomeric sheet, wherein the elastomeric sheet forms a seal between the control chamber and the fluid flow path to restrict fluid communication therebetween.

8. A device in accordance with claim 1, wherein the flexible seal further comprises:

an elastomeric plug, disposed in a wall of the fluid reservoir with a portion of the power transfer linkage extending through the elastomeric plug, the elastomeric plug being bonded to the power transfer linkage to form a seal thereon, and configured to elastically flex with the power transfer linkage as the power transfer linkage moves during use.

9. A device in accordance with claim 8, wherein a portion of the flexible seal stretches on one side of the power transfer linkage and a portion compresses on an opposite side of the power transfer linkage.

* * * * *